United States Patent [19]
Weigum

[11] Patent Number: 5,462,547
[45] Date of Patent: Oct. 31, 1995

[54] TROCHANTER STABILIZATION DEVICE

[75] Inventor: Hans Weigum, Niederdorf, Switzerland

[73] Assignee: Synthes (U.S.A.), Paoli, Pa.

[21] Appl. No.: 886,235

[22] Filed: May 21, 1992

[30] Foreign Application Priority Data

May 30, 1991 [CH] Switzerland ............... 01602/91

[51] Int. Cl.⁶ ............................................. A61B 17/56
[52] U.S. Cl. ............................................. 606/65; 606/67
[58] Field of Search ................... 606/65, 66, 67, 606/68, 72, 73, 104; 411/461, 462, 463, 544, 531, 545

[56] References Cited

U.S. PATENT DOCUMENTS

| | | | |
|---|---|---|---|
| 3,489,143 | 1/1970 | Halloran | 606/67 |
| 3,554,193 | 1/1971 | Konstantinou | 606/65 |
| 3,842,825 | 10/1974 | Wagner | 606/66 |
| 4,101,985 | 7/1978 | Baumann | 606/67 |
| 4,438,762 | 3/1984 | Kyle | 606/65 |
| 4,565,193 | 1/1986 | Streli | 606/67 |
| 4,628,923 | 12/1986 | Medoff | 606/65 |
| 4,973,332 | 11/1990 | Kummer | 606/65 |
| 4,988,350 | 1/1991 | Herzberg | 606/65 |
| 5,087,260 | 2/1992 | Fixel | 606/65 |

*Primary Examiner*—Michael A. Brown
*Attorney, Agent, or Firm*—Davis Hoxie Faithfull & Hapgood

[57] ABSTRACT

A device for treating fractures of the neck and shaft of bones such as the femur, which includes a sleeve strap and a trochanter stabilization plate, and is designed so that the stabilization plate can be positioned over a previously installed sleeve strap.

13 Claims, 5 Drawing Sheets

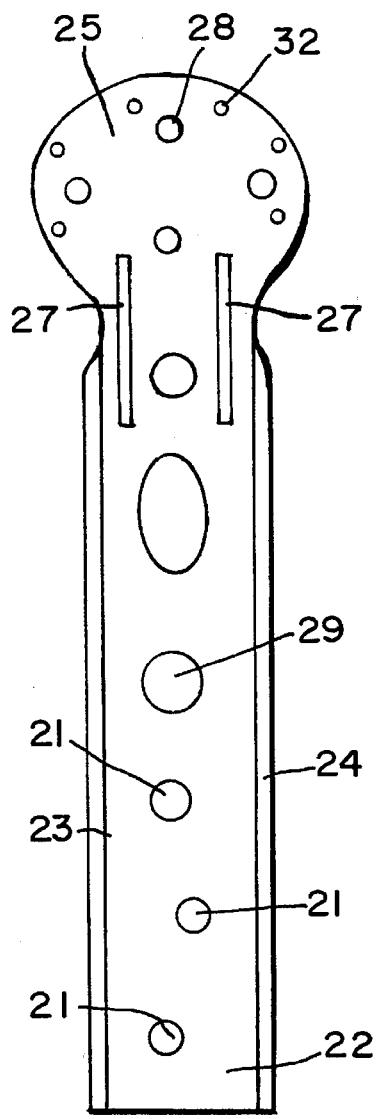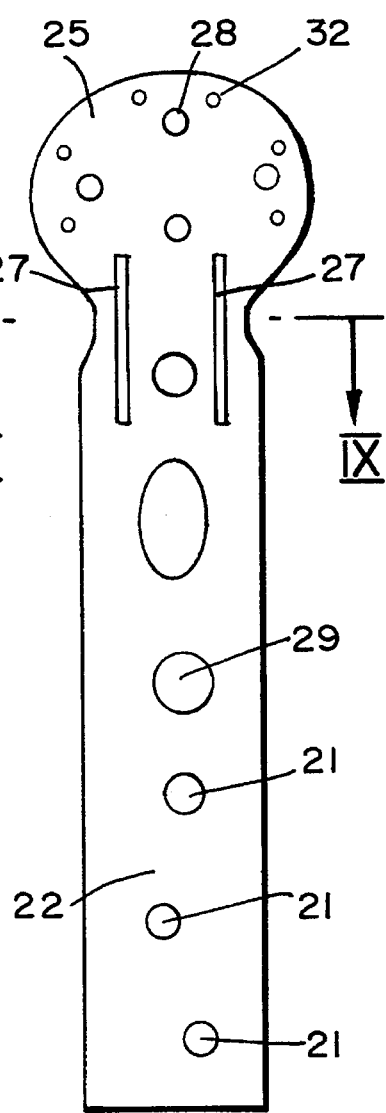
Fig. 2   Fig. 3   Fig. 4

TROCHANTER STABILIZATION DEVICE

FIELD OF THE INVENTION

This invention relates to a device for the treatment of fractures of bones having a shank and a joint area. In particular, it relates to a device for the treatment of fractures of the neck of the femur, accompanied by fracture of the trochanter.

BACKGROUND OF THE INVENTION

Devices for treating femur fractures are known. See, for example, EP-A2 0 347 874, which has a conventional sleeve strap and a trochanter stabilization plate that can be separably connected with the sleeve strap. However, a disadvantage of this device is its interlocking construction, which makes it necessary to attach the trochanter stabilization plate directly to the bone and to attach the sleeve strap over the trochanter stabilization plate, resting on the bone. In this obligatory sequence of the two components, the surgeon must make a decision right at the start whether or not to use a trochanter stabilization plate. Later installation of a trochanter stabilization plate, after a bone break has been treated with a sleeve strap, is no longer possible without completely removing the sleeve strap. In hospital practice it is desirable that the decision on whether or not to use a trochanter stabilization plate be made as late as possible.

SUMMARY OF THE INVENTION

In accordance with the present invention, a device is provided for treating a broken bone, particularly a femur fractured in the neck area, which device is easy to manufacture and assemble, and which is universally applicable according to individual needs.

Specifically, the invention provides a device of the kind described comprising a sleeve strap having a bone attachment leg for application to the shank of the bone to be treated and a sleeve positioned at an angle to the bone attachment leg for insertion into the joint area of the bone. The leg has apertures, e.g. screw holes, for facilitating attachment to the bone shank. Combined with the sleeve strap is a trochanter stabilization plate for separable attachment to the bone attachment leg of the sleeve strap. The trochanter stabilization plate has a longitudinal part for positioning parallel to the bone attachment leg of the sleeve strap and a trochanter support part, connected to the longitudinal part. The longitudinal part has its edges bent in to form a track for receiving the bone attachment leg, and apertures, corresponding to apertures on the bone attachment leg, for accommodating the same bone screws or other attachment devices.

The invention further comprises a trochanter support plate having the characteristics described.

The principal advantage achieved by the invention is that the invention permits subsequent assembly of the trochanter stabilization plate on an already installed sleeve strap. To eliminate the need for completely loosening the position of an already mounted sleeve strap, at least one attachment aperture of the shaft portion of the trochanter stabilization plate for the attachment device, e.g. the bone screw, is drilled completely through. It is advantageous to choose the screw hole closest to the bone attachment screw to be inserted into the trochanter, but one of the other screw holes can be chosen. The fact that the head of the bone attachment screw can pass through the screw hole makes it unnecessary to completely loosen the sleeve strap for later assembly of the trochanter stabilization plate.

To reinforce the trochanter stabilization plate against bending in the medio-lateral plane, and at the same time to prevent the trochanter stabilization plate from turning toward the sleeve strap, the edges of the longitudinal shaft portion are bent sideways in at least one area, so that a track is created that can be pressed or snapped onto the sleeve-strap bone attachment leg lying on the bone. Through the firm position thereby achieved, friction corrosion of the type that can occur with prior combination devices can be prevented.

In a preferred embodiment of the invention, the longitudinal shaft portions of the trochanter stabilization plate and the bone attachment strap of the sleeve strap are in the shape of the segment of a hollow cylinder, in order to achieve the best possible adaptation to the anatomy of the bone. The hollow cylindrical design of the trochanter stabilization plate and the bone attachment strap also improves resistance to bending.

Advantageously, the trochanter stabilization plate designed as an outer track for the bone attachment strap of the sleeve strap is constructed as a flexible clip that encloses the bone attachment leg of the sleeve strap like a spring, just with the ends of its edges. This spring-like clip action makes the fitting of the two meshing parts less critical.

The edges of the longitudinal shaft portion of the trochanter stabilization plate are bent at an angle $\alpha$ of between about 1° and about 5°, preferably between about 2° and about 4°, in relation to the strap edges, which permits a larger radius than with the corresponding side strap edges on the sleeve strap. The advantages here relate to materials and processing, since the sheet metal used for the trochanter stabilization plate has greater firmness with a larger radius and can therefore be bent with less specific stress. There are also construction advantages. In tolerance-critical cases with close fit, when the edges are bent the side contact point remains at the same place, which facilitates a maximum bending lever arm and hence a minimum bending force; the bending of the edges thereby creates an improved size tolerance of the device according to the invention.

In another aspect of the invention, the corresponding attachment perforations of the bone attachment leg are countersunk and the corresponding attachment apertures of the shaft portion have a corresponding boss that fits into the countersink. By means of this positive engagement of the two plates, an axial slippage of the two plates against each other is prevented. This effect is further reinforced by the attachment devices inserted through the corresponding attachment apertures. A rigid connection of the two plates is extremely important in order to prevent friction corrosion. In addition, this also means less height from the manufacturing point of view. Moreover, the screw heads project from the combined device according to the invention by only about the thickness of the sheet metal. In a good fit of the counterbores and recesses, the possibility of a dynamic compression is maintained.

The introduction of reinforcement ribs, preferably running longitudinally, in the area of the trochanter support sections extending into the area of the shaft portion, reinforces the stiffness of the trochanter stabilization plate. To achieve uniform stiffness over the entire length of the trochanter stabilization plate, the ribs and the bent edges should overlap. A bulged or countersunk hole (possibly in the form of an elongated slot) for an anti-rotation screw to be inserted directly above the bone attachment screw has an additional stiffening effect that can act as an alternative or a supplement to the ribs.

In contrast to prior devices with similar designs in which the surfaces of contact between the sleeve strap and the trochanter stabilization plate had to be coordinated, in the device according to the invention, a uniform length of the trochanter stabilization plate, for example with four attachment apertures, is sufficient, regardless of the length of the corresponding portion of the sleeve strap used. For the trochanter support portion, particularly if it is designed to be adaptable, one length and one shape suffice, so that it is possible to use a single standardized trochanter stabilization plate for all applications.

This advantage, together with the possibility of manufacturing the device out of sheet metal, permits extremely low-cost manufacturing and high output. Because the stiffness of the trochanter stabilization plate is achieved through its curvature, its bent edges, and, preferably, its ribs, a relatively thin sheet metal can be used in the manufacturing process. This, in turn, permits the surgeon appropriately to bend the trochanter support parts during the operation in order to achieve a better fit with the trochanter.

BRIEF DESCRIPTION OF THE DRAWINGS

The invention will be further described with reference to the accompanying drawings, in which:

FIG. 2 is a front elevated view of the trochanter stabilization plate of FIG. 1;

FIG. 3 is a side view of the trochanter stabilization plate of FIG. 1;

FIG. 4 is a rear view of the trochanter stabilization plate of FIG. 1;

DETAILED DESCRIPTION OF THE INVENTION

Referring to FIGS. 1–5, the device according to the invention consists essentially of a conventional sleeve strap 10, as used in the treatment of femur-neck fractures, and a trochanter stabilization plate 20.

Figure 7:
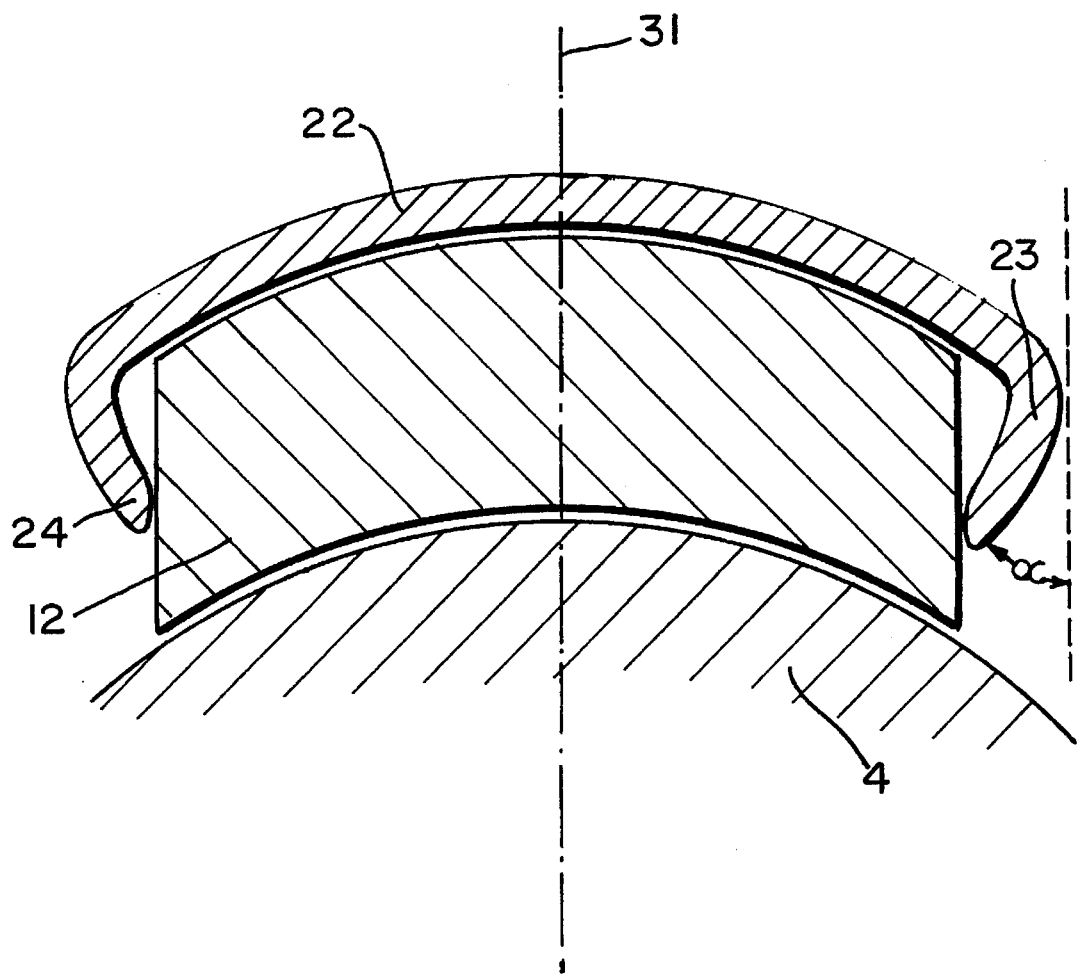
FIG. 7 is a cross-section along line VII—VII of FIG. 5.
Figure 8:
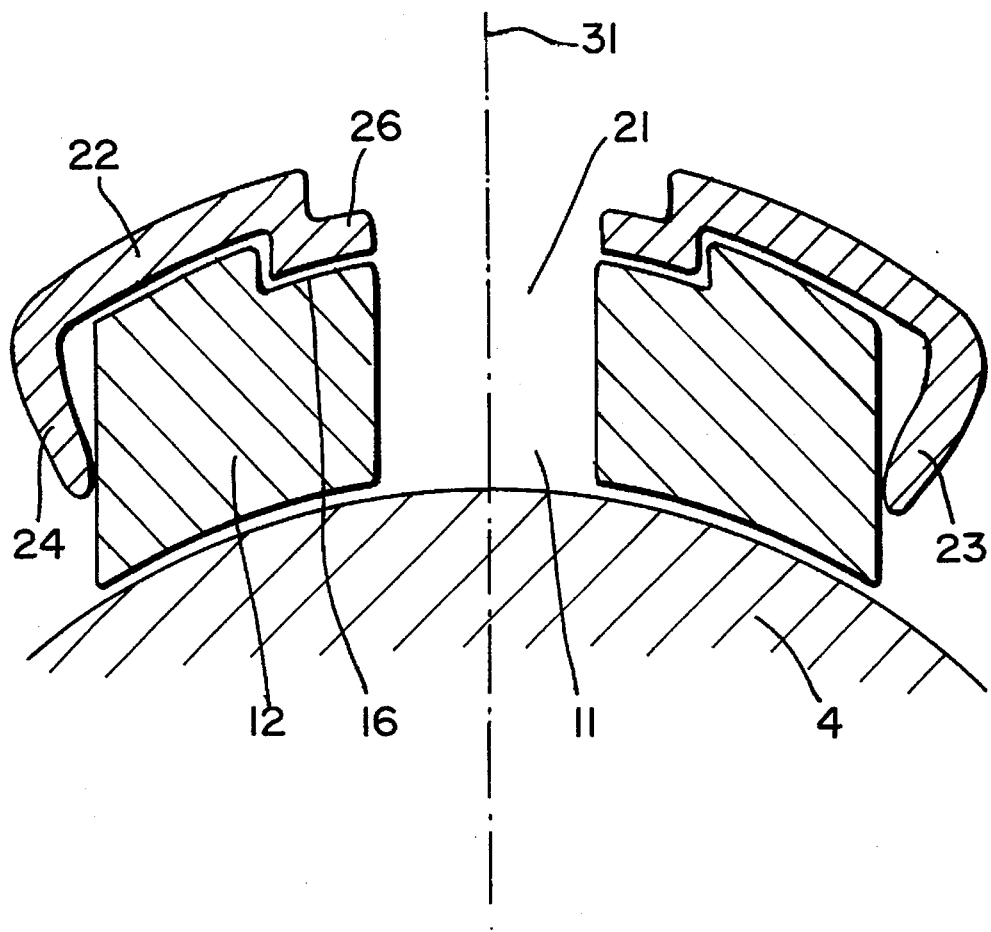
FIG. 8 is a cross section along line VIII—VIII of FIG. 5.

The sleeve strap 10 consists of a bone attachment leg 12, which can be connected with the femur shaft 4, and which runs parallel to the longitudinal axis 3 of the femur shaft 4. Leg 12 has a number of attachment apertures 11. Sleeve strap 10 also has a sleeve 13, at an angle to the leg 12, with a hole 17, through which a bone screw 14, or a functionally similar bone pin, can be inserted. The attachment apertures 11 are preferably offset, and countersunk as at 16 (FIG. 8). To immobilize the bone attachment strap 10, conventional attachment screws 30 are used. For better anatomical adaptation to the curved bone surface, the bone attachment leg 12 of sleeve strap 10 is designed as a hollow cylinder sector adapted to the shaft of the bone (FIGS. 7 and 8).

Figure 1:
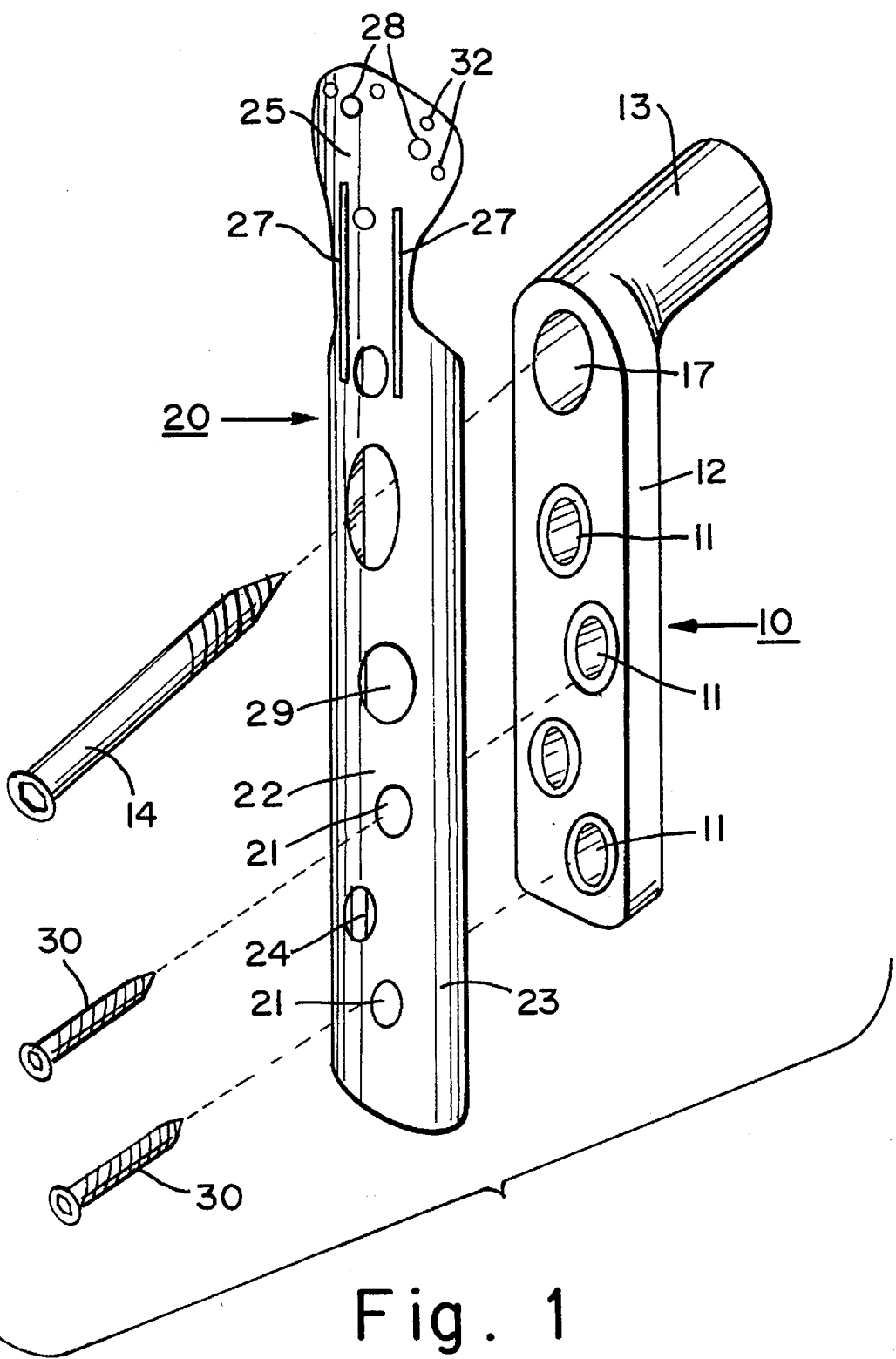
FIG. 1 is a perspective exploded view of a device according to the invention.
Figure 5:
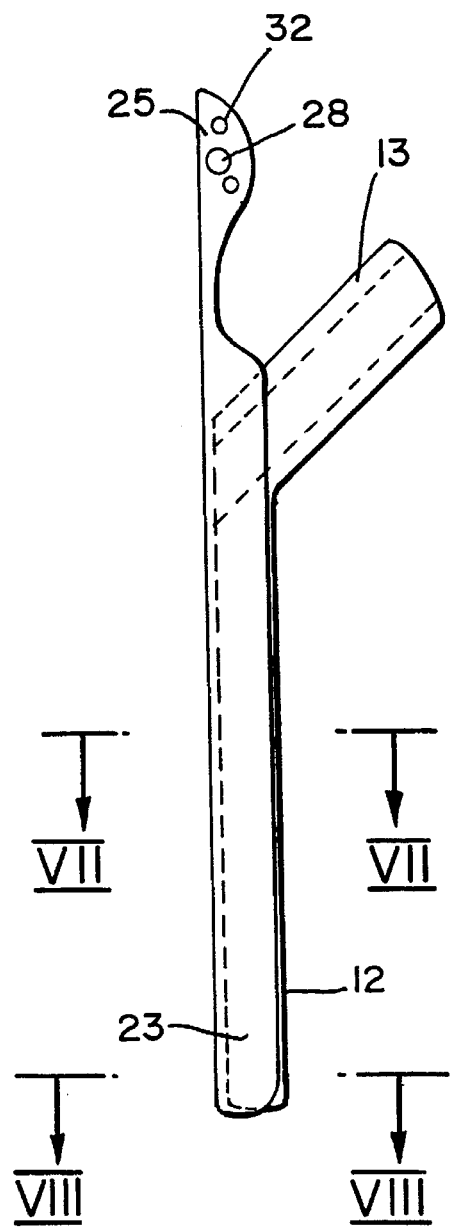
FIG. 5 is a side view of the sleeve strap assembled with the trochanter stabilization plate acting as a track in accordance with the invention.
Figure 6:
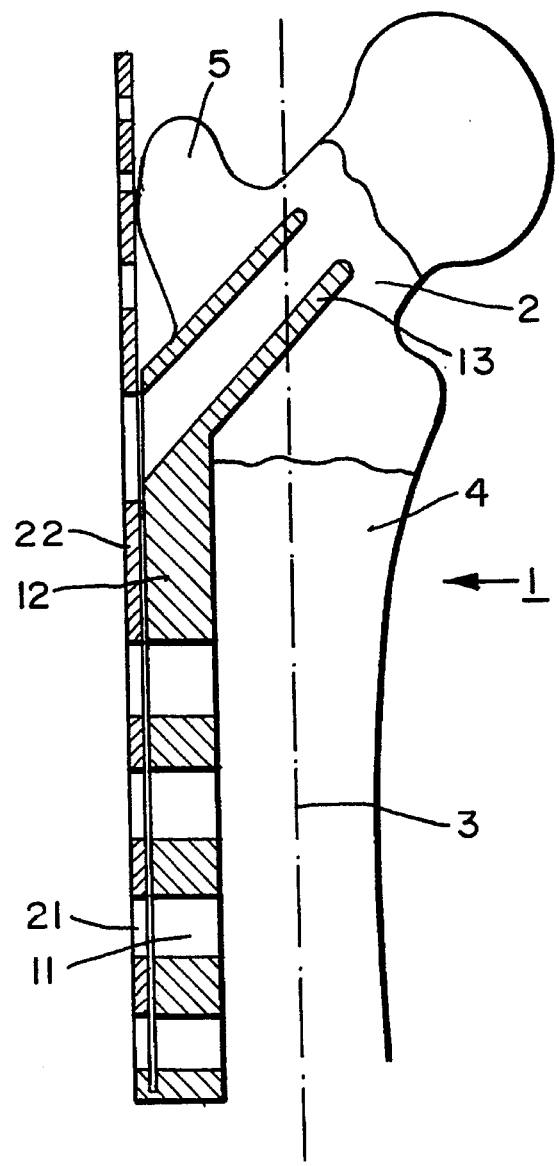
FIG. 6 is a vertical section through the device according to FIG. 5, put together and positioned on a femur.

The sleeve strap 10 may be implanted using conventional operating techniques. By means of appropriate aiming devices a hole is made, in the latero-medial direction, from beneath trochanter 5 through the center of the femur neck 2. In this hole the sleeve 13 of the sleeve strap 10 can be inserted. Lastly, the sleeve strap 10 with its leg 12 is screwed onto the shaft of the femur 4 (this situation is illustrated in FIG. 6).

The second component of the device according to the invention consists of a trochanter stabilization plate 20 composed essentially of a longitudinal shaft part 22 and a trochanter support part 25 connected therewith.

The longitudinal shaft part 22, which runs parallel to bone attachment leg 12 of sleeve strap 10, has a number of attachment apertures 21, which are aligned with the attachment apertures 11 of bone attachment leg 12. To achieve a stable connection of the trochanter stabilization plate 10 with the sleeve strap 10, the attachment apertures 21 of shaft part 22 have a boss 26 (FIG. 8) that accords with and engages the countersink 16 of the attachment apertures 11.

Shaft part 22 has an outer side and an inner side that faces the bone or the sleeve strap positioned on the bone. Like the bone attachment leg 12 of sleeve strap 10, the shaft part 22 is designed as a sector of a hollow cylinder (FIGS. 7 and 8). The side edges 23 and 24 of shaft part 22 are bent toward the inner side, so that an outer track for the adjacent bone attachment leg 12 of sleeve strap 10, resting on the bone, is formed. Together with shaft part 22, as shown in FIG. 7, edges 23 and 24 form an angle α of approximately 3° (relative to the plane of symmetry 31), so that a flexible clamp is formed which, acting like a spring, holds the bone attachment leg 12 of sleeve strap 10.

A cranially oriented trochanter support part 25 is attached to the caudally positioned shaft part 22. This trochanter support part 25 is shaped like a small basket, and has a number of attachment apertures 28 having a diameter of about 4 mm. In addition to the attachment apertures 28, there is a row of smaller apertures 32, approximately 3 mm in diameter, along the edge. These smaller apertures 32 serve for the alternative or supplemental use of wiring. The larger attachment apertures 28 are not suitable for this purpose, because they are not in a good position for it. Also, because of their countersinks, they inevitably have sharp edges that may cut the wiring.

Figure 9:
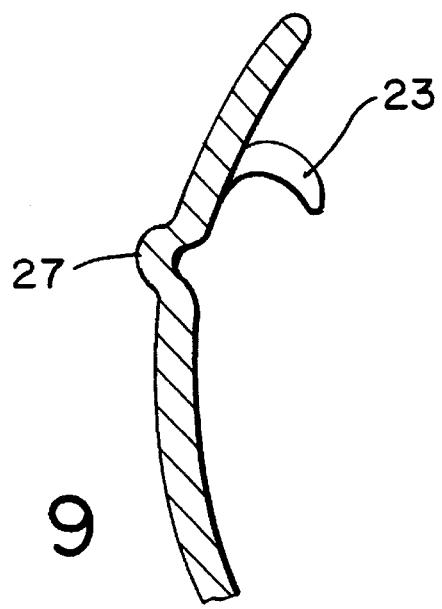
FIG. 9 is a cross section along line IX—IX of FIG. 4.

As illustrated in FIG. 9, two longitudinal ribs 27 are provided for the reinforcement of the transition area between shaft part 22 and trochanter support part 25, which ribs extend to the shaft part 22.

Bone attachment leg 12 of strap 10 is inserted into the outer track-like shaft part 22 of trochanter stabilization plate 22, and the mutually corresponding attachment apertures 11 and 21 aligned, so that by means of screws 30, which serve as attachment devices, both components of the device according to the invention are connected with bone 1 using the same screws. The trochanter support part is deformable, so that it can be adjusted during the operation to the trochanter geometry and attached to a trochanter 5 by means of appropriate screws (not illustrated) inserted into the attachment apertures 28.

Because one of the attachment apertures 29 of shaft part 22 is designed to be completely penetrable by the attachment device 30 to be inserted therein, that is, it is larger than the other attachment perforations 21, the trochanter stabilization plate 20 can be mounted on a sleeve strap 10 already immobilized on the bone, without any need to loosen the sleeve strap 10.

More specifically, if, during the operation the surgeon has already attached the leg 12 of the strap 10 to the bone, and then decides that a trochanter stabilization plate is necessary, he will proceed as follows:

a. All the fixation screws attaching the leg 12 to the bone are removed except that corresponding to the oversized hole in the stabilization plate. This one screw is sufficient to hold everything in place during the procedure.

b. The stabilization plate is applied over the sleeve strap. The head of the screw remaining fixed in the bone is accommodated by the oversized hole.

c. The remaining fixation screws are applied through the stabilization plate and the sleeve strap securing both to the bone.

d. If necessary, during application of the additional screws (step (c)), the screw corresponding to the oversized hole can be adjusted (loosened or tightened).

Providing the oversized hole avoids any problems caused by the head of the corresponding screw in the leg 12 interfering with the fit of the plate, and permits the adjustments referred to in step (d).

Because of its structural stiffness, the trochanter stabilization plate 20 can be manufactured out of a fairly thin sheet metal. Stainless steel is preferable.

What is claimed is:

1. Device for treating a bone having a shank and a joint area with a fracture in the joint area comprising a sleeve strap having a bone attachment leg for application directly to the shank of the bone, said bone attachment leg having apertures for facilitating attachment to the bone, and a sleeve, positioned at an angle to the bone attachment leg for receiving a connecting element for insertion into the joint area, in combination with a trochanter stabilization plate for separable connection with the bone attachment leg of said sleeve strap on the side of said attachment leg remote from the bone, said plate having a longitudinal part for positioning parallel to the bone attachment leg and a trochanter support part connected to said longitudinal part, said longitudinal part of the plate having its edges bent to form tracks for receiving the bone attachment leg and apertures corresponding to the apertures in the bone attachment leg whereby the plate and the bone attachment leg can be connected to the bone shank by common attachment devices.

2. Device according to claim 1, wherein the longitudinal part of the trochanter stabilization plate and the sleeve strap bone attachment leg have the shape of a sector of a hollow cylinder.

3. Device according to claim 1, wherein the trochanter stabilization plate is flexible and spring-like.

4. Device according to claim 3, wherein the edges of the longitudinal part of the trochanter stabilization plate form, in relation to the plane of symmetry of the trochanter stabilization plate an angle $\alpha$ of between about 1° and about 5°.

5. Device according to claim 4, wherein $\epsilon$ is between about 2° and about 4°.

6. Device according to claim 1, wherein the attachment apertures of the bone attachment leg are countersunk, and the corresponding attachment apertures of shaft part have corresponding recesses.

7. Device according to claim 1, wherein the trochanter support part has longitudinal reinforcement ribs.

8. Device according to claim 7, wherein the trochanter support part extends to the shaft part.

9. Device according to claim 1, wherein at least one of the attachment apertures of the shaft part is enlarged to completely accommodate an attachment device introduced therein.

10. Device according to claim 1, wherein the trochanter stabilization plate has attachment apertures.

11. Device according to claim 1, wherein the trochanter stabilization plate is steel between about 1.25 and about 1.85 mm, thick.

12. Device according to claim 11, wherein the plate is between about 1.35 mm and about 1.7 mm thick.

13. A method of treating fractures in the neck and shank of a bone having a shank portion and a joint portion comprising applying a sleeve strap having a leg part and a sleeve part to the bone with the leg part attached to the bone shank and the sleeve part extending into the joint and applying a trochanter stabilization plate having a trochanter support part and a shaft part with edges turned into the sleeve strap by snapping the turned in edges of the sleeve shaft part around the edges of the leg of the sleeve strap and securing both the sleeve strap and the stabilization plate to the shank of the bone with bone attachment devices.

* * * * *